United States Patent [19]

Cerami et al.

[11] Patent Number: 4,705,845
[45] Date of Patent: Nov. 10, 1987

[54] PROCESS FOR SULPHATION AND PHOSPHORYLATION OF PROTEINS AND PEPTIDES

[75] Inventors: Anthony Cerami, Flanders, N.J.; Sandor Pongor; Michael Brownlee, both of New York, all of N.Y.

[73] Assignee: Rockefeller University, New York, N.Y.

[21] Appl. No.: 904,056

[22] Filed: Sep. 5, 1986

Related U.S. Application Data

[60] Continuation of Ser. No. 697,134, Feb. 1, 1985, abandoned, which is a division of Ser. No. 442,492, Nov. 17, 1982, Pat. No. 4,534,894.

[51] Int. Cl.[4] .................... A61K 37/26; C07K 7/40; C07K 15/00
[52] U.S. Cl. .................... 530/305; 530/303; 530/304; 530/345; 530/404; 530/406; 530/408; 530/410
[58] Field of Search .............. 530/305, 408, 410, 303, 530/304, 345

[56] References Cited

U.S. PATENT DOCUMENTS 3,361,574  1/1968  Paulsen ............................ 530/378 X
4,322,344  3/1982  Chen et al. ...................... 530/410 X
4,534,894  8/1985  Cerami et al. ................... 530/408 X

OTHER PUBLICATIONS

Biochim–Biophys. ACTA 5, 89–97 (1950), Fraenkel–Contrat et al.

*Primary Examiner*—Howard E. Schain
*Attorney, Agent, or Firm*—Felfe & Lynch

[57] ABSTRACT

A process for sulphation and phosphorylation of a protein or peptide comprising contacting said protein or peptide with sulphuric or phosphoric acid in the presence of a non-aqeuous apolar organic solvent and contacting the resultant solution with a dehydrating agent is disclosed. Non-aggregating insulin products with bioactivity may be prepared by this process.

8 Claims, No Drawings

PROCESS FOR SULPHATION AND PHOSPHORYLATION OF PROTEINS AND PEPTIDES

The present invention was wholly or partially made with funds provided by the Department of Human Health and Services under Grant No. NIH-AM 00589. Accordingly, the United States Government has certain rights in this invention.

This is a continuation of application Ser. No. 697,134, filed Feb. 1, 1985, now abandoned, which is a division of Ser. No. 442,492, now U.S. Pat. No. 4,534,894, filed Nov. 17, 1982.

This invention concerns a novel method for sulphating and phosphorylating proteins and peptides. By means of this method non-aggregating insulin derivatives may be prepared.

The discovery that insulin is effective in controlling hyperglycemia associated with diabetes was followed by active research efforts directed towards characterizing the chemical nature of the molecule and developing improved insulin products and modes of administration.

Recently an open loop pump delivery system for administering insulin has been developed. This system is capable of delivering a steady concentrated supply of insulin, but its use for this purpose has been limited by the tendency of commercially available insulin to aggregate and consequently clog the system. This tendency of insulin to aggregate has other serious implications. It has been observed, for example, that aggregated insulin solutions lead to an adverse side effect, amyloidosis, in laboratory animals and may be more immunogenic than non-aggregated preparations. Therefore, a method for modifying insulin to make it non-aggregating in concentrated preparations has been sought. It is known that sulphated insulin is non-aggregating and can be used in the open loop delivery system (W.D. Lougheed et al., Diabetologia lg, l-g (1980)). Sulphated insulin is currently prepared by contacting insulin with cold ($-18°$ C.), sulphuric acid (Reitz, H. C. et al., *Ind. Eng. Chem.,* 36 1140 (1944)) or with pyridine chlorosulphonic acid (Reitz, H.C. et al., *J. Amer. Chem. Soc.,* 68, 1031 (1946)). The phosphoric derivative is currently prepared by contacting insulin with phosphoric anhydride in phosphoric acid at room temperature for several days (Fraenkel-Conrat, J. et al., *Biochim et Biophys. Acta,* 5 89 (1950)). However, the harsh reaction conditions employed in these procedures lead to a product of significantly reduced biological activity. Accordingly, a search was undertaken for a method of sulphating and phosphorylating insulin which leads to a product of high biological activity. It was found that a method employing sulphuric acid or phosphoric acid and a dehydrating agent in a non-aqueous apolar organic solvent effectively modified insulin in a non-destructive manner. Moreover, this method is of significant use in sulphating and phosphorylating other proteins and peptides under mild reaction conditions.

SUMMARY OF THE INVENTION

Accordingly, it is a principal object of the present invention to provide a novel method for sulphating and phosphorylating proteins and peptides.

It is a particular object of the present invention to provide a method for making a sulphated insulin product which is non-aggregating at high concentrations (higher than currently available) but which retains high hypoglycemic activity.

It is another object of the present invention to provide a method for making a phosphorylated insulin product which is non-aggregating and is bioactive. Such biological activity was not available in any phosphorylated insulin previously prepared.

In accordance with the present invention, a protein or peptide to be modified is contacted with a known amount of sulphuric or phosphoric acid in a non-aqueous apolar organic solvent and is then contacted with a suitable dehydrating agent. In a preferred embodiment of the present invention, insulin is contacted with sulphuric acid in dimethyl formamide (DMF), dioxane, or dimethyl sulphoxide, most preferably dimethyl formamide and is then contacted with a dehydrating agent preferably a N,N'-carbodiimide chlorosulphonic acid or sulphurtrioxide in a complexing agent, preferably pyridine. A similar method is also disclosed for preparation of non-aggregating phosphorylated insulin.

DETAILED DESCRIPTION OF THE INVENTION

In the process of the present invention, a peptide, preferably insulin, is contacted with sulfuric acid or phosphoric acid in an apolar organic solvent followed by addition of a determined amount of dehydrating agent.

Peptides which may be sulphated or phosphorylated by the present method include those which contain amino acids with hydroxyl side chains. In porcine insulin, for example, there are a total of 9 hydroxyl groups located on the amino acids serine, threonine and tyrosine. The sulfated product is a mixture of isomers which differ according to the number and location of hydroxyl groups sulfated. Isomers bearing the same number of sulphate groups will co-migrate on electrophoresis. Electrophoretic analysis of insulin sulphated by the present invention shows six bands corresponding to these different products.

Preferred apolar organic solvents of the present invention include dimethyl formamide, dioxane and dimethyl sulphoxide, most preferably dimethyl formamide and mixtures thereof. In these neutral organic solvents lower amounts of acid may be used than are required in the aqueous solvents of prior methods. Undesirable biodegrading side reactions are thus avoided.

The dehydrating agents of the present invention comprise N,N'-carbodiimides, acid halogenides and anhydrides. Preferred carbodiimides comprise N,N'-dicyclohexyl carbodiimide, N-ethyl N'-dimethylaminopropyl-carbodiimide and N-cyclohexyl-N'morpholinoethyl carbodiimide, most preferably N,N'-dicyclohexyl carbodiimide. Preferred acid halogenides for sulphation are halosulphonic acids, most preferably chlorosulphonic acid. Preferred acid halogenides for phosphorylation are phosphoryl halides, most preferably phosphoryl chloride. Sulphur trioxide may also be used as a dehydrating agent. Sulphur trioxide-pyridine complex and sulphur trioxide-trimethyl amine complex are preferred agents. In the process of the present invention the extent of sulphation or phosphorylation may be controlled by varying the amount of dehydrating agent employed in the reaction. For example, in preferred embodiments of the present invention wherein N,N'-carbodiimide is employed as dehydrating agent for the sulphation of insulin, the extent of sulphation of insulin can be limited to three or less sulphates by limiting the amount of N,N'-carbodiimide used in the reaction.

The following examples are provided to illustrate the method of the present invention but they are in no way meant to limit its scope.

EXAMPLE 1

Preparation of Sulphated Insulin 20 mg of porcine sodium insulin was dissolved in a mixture of 905 μl of dry dimethylformamide and 50 μl of concentrated sulfuric acid at 4° C. 80 mg. of N,N' dicyclohexyl carbodiimide (DCC) dissolved in 100 μl of DMF was added to this mixture and the solution was shaken overnight at 4° C. Cracked ice (approx. 1 g was added and the pH was adjusted to 7.5 with 10N NaOH. The solution was brought to 5 ml and centrifuged. The supernate was extensively dialysed against 0.05M ammonium bicarbonate, pH=7.5, and lyophilized.

Hypoglycemic potency of the modified insulin was measured as described in "The United States Pharmacopeia", Mark Publishing Co., Vol. 18, pp. 883-884 (1964). Bioactivity was 62% as compared to unmodified insulin.

The tendency of modified insulin to aggregate was assessed by measuring the turbidity of the solution. This method is based on the work of Leach and Scheraga (S. J. Leach and H. A. Scheraga (1964) J. Amer. Chem. Soc. 82, 4790-4792) who stated that absorbancy observed in insulin solutions between 350 and 600 nm is due to light scattering of aggregated particles. Briefly, 10 mg of sample was dissolved in 2 ml of isotonic phosphate buffered saline (PBS) and the solution was passed 50 times through a 3 cc plastic syringe (B-D Plastipak, Luer Lok Type) equipped with a 26G ⅜" hypodermic needle. After deaeration under vacuo for 60 min. 1 ml of this solution was diluted with 1 ml of PBS, and the turbidity was measured on a Hewlett Packard spectrophotometer type HP 8590, utilizing as a blank a non-aggregated sample diluted by 1 volume of 8M guanidine hydrochloride. Aggregation was measured by the difference in absorbance determined at 400 nm for the two samples. Non-aggregated samples gave absorbance values of 0 to 0.1 Absorbance Unit(A), Values above 0.3 were considered to be aggregated. Utilizing this assay the turbidity of this modified insulin dissolved in PBS was 0.08 A. In contrast unmodified porcine sodium insulin dissolved in distilled water has an absorbance of 0.51 A when treated according to the above procedure.

EXAMPLE 2

Sulphation of Insulin With Different Amounts of Dehydrating Agent

Example 1 was repeated with different amounts of N,N'-dicyclohexyl carbodiimide dissolved in 100 μl of dry dimethyl formamide added to 20 mg of porcine sodium insulin dissolved in the mixture of 950 μl DMF and 50 μl of concentrated sulphuric acid at 4° C.

The modified insulin samples were subjected to gel electrophoresis and densitometric evaluation. Briefly, gel electrophoresis was carried out by dissolving 2 mg of samples (sulphated or unmodified insulin) in 7M urea. 20 μl of this solution was analyzed by electrophoresis at pH-8.3 on polyacrylamide gels containing 25% w/v acrylamide and 0.15% w/v bis-acrylamide under the experimental conditions described by Davis (Baruch J. Davis (1964) Annals of the New York Academy of Sciences, Vol. 121, pp. 404-427). The gels were stained with Coomassie Brilliant Blue R and destained with 10% w/v trichloracetic acid. The $R_f$ values were calculated from the migration distances and were divided by the $R_f$ of unmodified insulin.

Densitometric evaluation was carried out by cutting the individual lanes of the gels and determining the scan with a Beckman ACTA III Spectrophotometer equipped with a type 198402 Gel Scanner Accessory, in silica cuvettes at 590 nm. The peaks were integrated manually and the relative quantities of the products were expressed as % of the total sum of the integral values.

The results of this experiment are summarized in Table 1.

TABLE 1

Quantitative Analysis of Sulphated Insulin Samples Denistometric Evaluation of Gel Electropherograms, Values Represent % of Total Material

|                          | 32 mg DCC | 96 mg DCC |
|--------------------------|-----------|-----------|
| Unmodified Insulin       | 65.3      | 9.6       |
| Modified Insulin Product 1 | 25.2    | 38.5      |
| Modified Insulin Product 2 | 6.5     | 30.1      |
| Modified Insulin Product 3 | 1.8     | 17.2      |
| Modified Insulin Product 4 | 1.2     | 2.3       |
| Modified Insulin Product 5 | 0.0     | 2.3       |

EXAMPLE 3

Sulphation of Insulin with Various Dehydrating Agents 100 mg of porcine sodium insulin was dissolved in the mixture of 4.75 ml of DMF and 0.25 ml of concentrated sulfuric acid at 4° C. The solution was divided into portions of 1 ml. The following reagents were subsequently added to individual tubes:

| Sample | Reagent added |
|--------|---------------|
| A | 57.5 mg of solid EDC (1-Ethyl-3-(3-Dimethylaminopropyl Carbodiimide) |
| B | 127 mg of solid CMC (1-Cyclohexyl-3(3-Morpholinoethyl) Carbodiimide). |
| C | 50 ul of chlorosulfonic acid diluted with 150 ul of DMF |
| D | 80 mg of Sulfur trioxide-pyridine complex |
| E | 80 mg of Sulfur-trioxide trimethylamine complex |

The samples were proceed as described in Example 1 (except that centrifugation was omitted), then subjected to gel-electrophoresis and densitometric quantitation. Results are summarized in Table 2.

TABLE 2

Quantitative Analysis of Sulphated Insulin Samples Denistometric Evaluation of Gel Electropherograms, Values Represent % of Total Material

|                          | EDC  | CMC  | ClHSO3 | SO3—Pyr | SO3—TA |
|--------------------------|------|------|--------|---------|--------|
| Unmodified Insulin       | 7.0  | 8.4  | —      | 6.3     | 8.2    |
| Modified Insulin Product 1 | 35.4 | 33.3 | —    | 14.5    | 34.4   |
| Modified Insulin Product 2 | 32.2 | 31.1 | 10.9 | 31.5    | 31.0   |
| Modified Insulin Product 3 | 16.7 | 18.2 | 35.0 | 34.2    | 20.9   |

TABLE 2-continued

Quantitative Analysis of Sulphated Insulin Samples
Denistometric Evaluation of Gel Electropherograms,
Values Represent % of Total Material

|  | EDC | CMC | ClHSO3 | SO3—Pyr | SO3—TA |
|---|---|---|---|---|---|
| Modified Insulin Product 4 | 6.3 | 4.8 | 49.0 | 7.5 | 6.2 |
| Modified Insulin Product 5 | 2.4 | 4.2 | 5.1 | 6.0 | 2.2 |

EXAMPLE 4

Phosphorylation of Insulin 20 mg of porcine sodium insulin was dissolved in the mixture of 950 μl of dry DMF and 50 μl of concentrated phosphoric acid prepared by heating 85% aqueous phosphoric acid to 150°–160° C. for about 4–5 hours. DCC (60 mg) dissolved in 100 μg of DMF was added to this solution, and the reaction mixture was shaken at 4° C. overnight. The sample isolated as described in Example 1 had a bioactivity of 85% as compared to unmodified insulin. Electrophoresis of the sample showed multiple bands bearing more negative charge than unmodified insulin.

EXAMPLE 5

Phosphorylation of Insulin 20 mg of porcine sodium insulin was dissolved in the mixture of 950 μl of dry DMF and 50 μl of phosphoric acid at 4° C. as described above. POCL$_3$ (5 μl diluted with 15 μl of DMF) was added and the reaction was carried out as described in Example 4. Electrophoresis of the sample showed 5 bands more negatively charged than unmodified insulin.

What is claimed is:

1. A method of phosphorylating a hydroxy containing protein or peptide comprising contacting said protein or peptide with phosphoric acid in a nonaqueous apolar organic solution and a dehydrating agent under conditions favoring phosphorylation of said hydroxy containing protein or peptide.

2. The method of claim 1 wherein said peptide is insulin.

3. The method of claim 1 wherein said solvent is dimethyl formamide.

4. The method of claim 1 wherein said dehydrating agent is a phosphoryl halide.

5. The method of claim 1 wherein said phosphoryl halide is phosphorylchloride.

6. A method as in claim 1, wherein said protein or peptide is insulin and said contact takes place at a temperature of about 4° C.

7. Phosphorylated proteins or peptides produced by the process of claim 1.

8. Phosphorylated insulin prepared by the process of claim 1.

* * * * *